United States Patent [19]

Horne, Jr. et al.

[11] 4,246,896
[45] Jan. 27, 1981

[54] INTRACERVICAL CUFF (ICC) FOR CONTRACEPTION AND PREVENTION OF VENEREAL DISEASE AND APPLICATOR THEREFOR

[75] Inventors: Herbert W. Horne, Jr., Framingham; Joseph D. Gresser, Brookline, both of Mass.

[73] Assignee: Dynatech Corp., Burlington, Mass.

[21] Appl. No.: 955,872

[22] Filed: Oct. 30, 1978

[51] Int. Cl.³ .............................................. A61F 5/46
[52] U.S. Cl. .................................. 128/130; 128/260
[58] Field of Search ............................ 128/127–131, 128/260

[56] References Cited

U.S. PATENT DOCUMENTS

| 2,564,177 | 8/1951 | Schmitt | 128/131 |
| 3,441,018 | 4/1969 | Schneider | 128/130 |
| 3,892,238 | 7/1975 | Banford et al. | 128/260 |
| 4,146,024 | 3/1979 | Shroff | 128/131 |

FOREIGN PATENT DOCUMENTS

| 137447 | 5/1934 | Austria | 128/131 |
| 204392 | 11/1908 | Fed. Rep. of Germany | 128/130 |
| 960761 | 3/1957 | Fed. Rep. of Germany | 128/130 |

*Primary Examiner*—Lawrence W. Trapp
*Attorney, Agent, or Firm*—Cesari and McKenna

[57] ABSTRACT

A two-stage device for use within the canal of the cervix of the uterus for the dual and simultaneous purposes of venereal disease prevention and of contraception by prohibiting the migration of sperm through the cervical canal. The two-stage device will consist of (Part A) an insertable member which will be inserted into and be maintained within the cervical canal to which (Part B) a temporary member, effective for upward of a year, can be attached easily with a minimum of discomfort to the patient. [Either or both parts of this two-stage device (at present most probably the temporary part) can incorporate metals such as copper, silver, or others, or suitable compounds thereof, and also spermicidal and pathogenocidal agents, steroids or other drugs.]

A unique feature of the invention is its placement within the cervical canal rather than in the fundus or vagina. Part A of the device is designed for semipermanent placement within the cervical canal; its main structural function is to act as a support for Part B which is designed for facile and comfortable removal and replacement and which contains the active agents possibly but not necessarily contained within a slow release matrix.

A second unique feature of the invention is the use of magnets to attach Part B to Part A.

23 Claims, 6 Drawing Figures

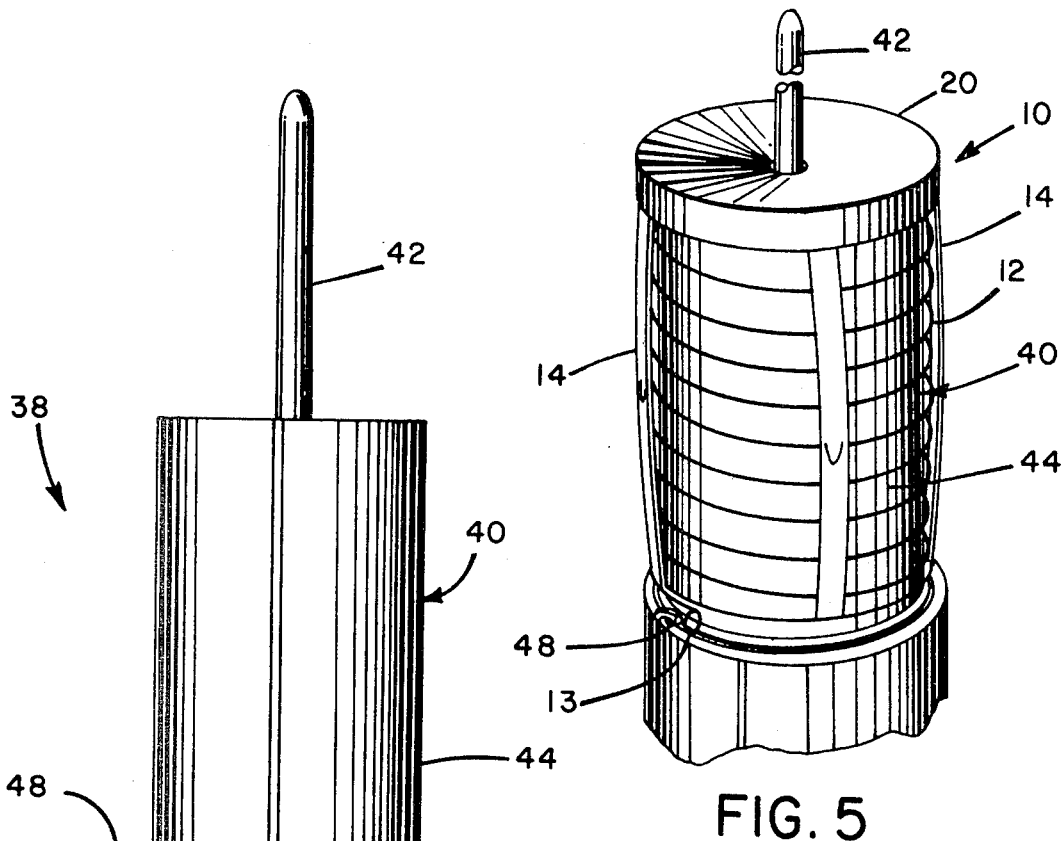
FIG. 4
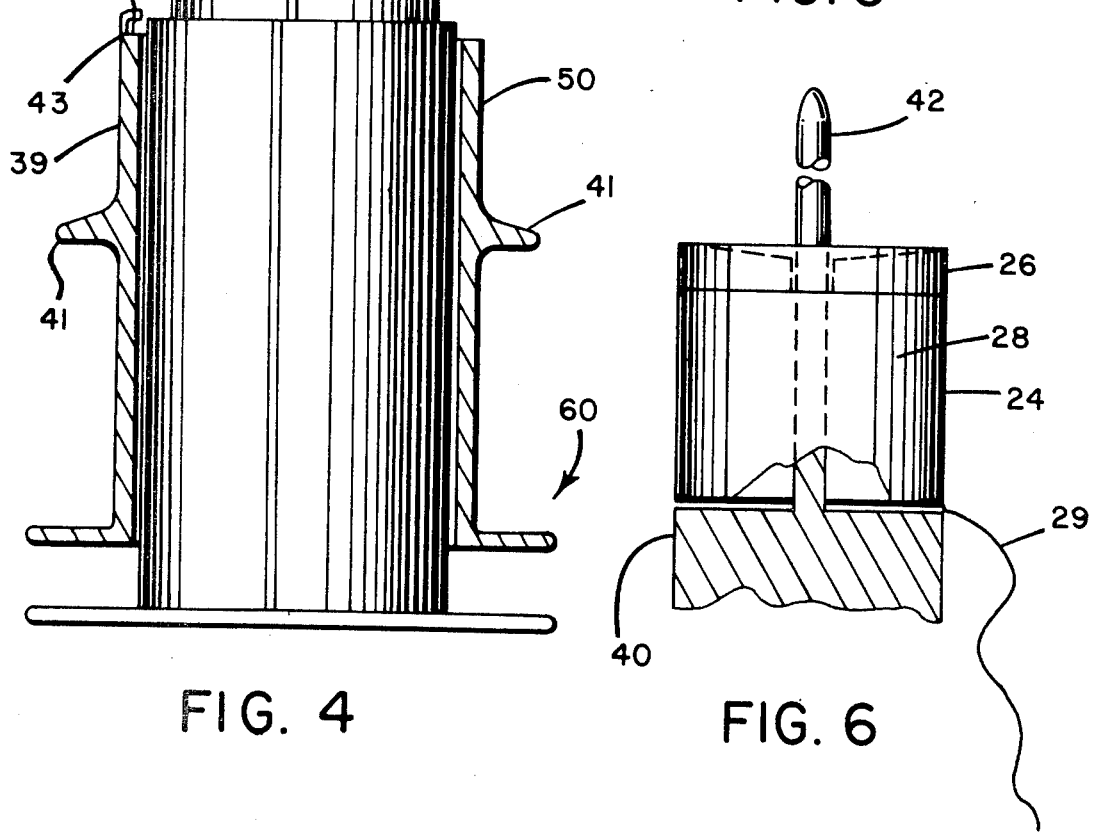
FIG. 5
FIG. 6

INTRACERVICAL CUFF (ICC) FOR CONTRACEPTION AND PREVENTION OF VENEREAL DISEASE AND APPLICATOR THEREFOR

DESCRIPTION OF THE PRIOR ART

The prior art involves two technologies: (1) incorporation of biologically active agents into solid or paste-like polymeric excipients for the purpose of sustaining delivery of those agents for periods longer than otherwise possible and (2) fabrication of various polymeric materials and metals into devices for insertion into the human uterine fundus and/or vagina for the prevention of pregnancy.

SUSTAINED RELEASE TECHNOLOGY

Devices for the controlled and continuous delivery of an active agent from a polymer excipient are known to the prior art. One group of such devices are best termed reservoir devices, characterized by a reservoir of the drug surrounded by a wall. The drug may be present separately or may be contained within a carrier permeable to the drug and in which the drug has limited solubility. The wall of the device permits passage of the drug as by diffusion and it is this step which controls the rate of drug release to the environment. U.S. Pat. No. 3,977,404 describes one such device utilizing a wall permeable to external fluid and permeable to drug via microporous openings to the environment. Another reservoir device described in U.S. Pat. No. 3,967,519 utilizes a reservoir formed of a drug carrier permeable to the drug in which the drug has limited solubility. In this case also, the wall is less permeable to the drug than is the carrier and is the rate controlling barrier to release. All of these devices can be designated to release drug within a body orifice; the object of U.S. Pat. No. 3,977,404 can also be used under an eyelid.

A number of devices all operating on the principle of drug diffusion through a wall or membrane permeable to the drug have been patented. Included are U.S. Pat. No. 3,961,628, which uses a nonbiodegradable polymer wall; U.S. Pat. No. 3,988,262, also of this type, may be used for anal or uterine drug delivery. U.S. Pat. No. 3,948,254 also claims a drug in a permeable carrier surrounded by an even less permeable wall. Permeability of the wall usually has been controlled by pore size or other openings in the wall but in U.S. Pat. No. 3,938,515, permeability is said to be controlled by addition of a small amount of polymeric material such as polyester (from a glycol and a dibasic acid), polyethylene glycol, etc.

Reservoir devices do not necessarily require a carrier for the drug. U.S. Pat. No. 3,279,996 describes a polysiloxane membrane enclosing the drug in dry solid or dissolved form. Controlled release is dependent on diffusion through the polymer wall of drug dissolved in tissue fluids, if originally dry, with a concentration gradient maintained by drug removal by body fluids or tissue absorption.

A second group of devices for maintaining sustained release have no external wall or membrane enclosing the drug. Instead, the active agent is blended with a polymeric excipient, the function of which is to retard release of the drug to the environment. In many cases, the carrier is biodegradable and will, in time, be absorbed by the body. This type of material releases its drug by either or both diffusion of drug through the matrix facilitated by entry of tissue fluids and continual exposure of new drug by erosion of the polymer surface. The biodegradability of these materials has made them useful as sutures, etc. U.S. Pat. No. 3,297,033 and U.S. Pat. No. 3,565,869 describe the use of polyglycolic acid for synthetic absorbable sutures, sponges, gauzes and prostheses. The former patent also claims that various materials including antibiotics may be incorporated into the polymer. Another patent, U.S. Pat. No. 3,371,069 describes the use of a partially esterfied poly-L-glutamic acid for absorbable sutures. Polylactic acid has also been patented for this use (U.S. Pat. No. 3,498,957).

Use of co-polymers for bioabsorbable materials has been described in several patents. U.S. Pat. No. 3,531,561 mentions high molecular weight polylactides polymerized with up to 15% of other monomers. Canadian Pat. No. 808,731 and Canadian Pat. No. 863,673 both describe use of up to 15% of comonomers such as glycolide or substituted glycolides, lactides or intermolecular cyclic esters in preparation of polylactic acid for use as absorbable sutures. U.S. Pat. No. 3,736,646 discloses an absorbable polymeric surgical element containing between 15-85 mole percent lactic acid. The remainder is mostly glycolic acid with small additions of a cyclic lactone.

These biodegradable materials can be used as carriers for biologically active materials. U.S. Pat. No. 3,737,521 describes the use of polyurethanes as an excipient in which the active agent is uniformly dispersed or dissolved throughout the polymer. Release is said to be a function of diffusion. A similar use of polylactic acid for drugs including among others narcotic antagonists, antipsychotics and antidepressives is disclosed in U.S. Pat. No. 3,773,919. This patent also describes sustained release using polylactic acid coated particles of drug, these particles being prepared by spray drying, fluid bed drying, or microencapsulation.

U.S. Pat. No. 3,887,699 outlines use of D(+), L(−) and poly-DL-lactic and polyglycolic acids for dispersion of drugs. Yolles describes (J. H. R., Woodland and S. Yolles; *J. Med. Chem.*, 16, 897; 1973), delivery of the narcotic antagonist cyclazocin and naltrexone. (S. Yolles, T. D. Leafe, J. H. R. Woodland, F. S. Meyer; *J.Pharm. Sci.*, 64, 349; 1975.)

Poly-L-lactic acid has been tested as a biodegradable carrier for the contraceptive steriod levenorgestrel at 33 w% loading in the matrix (J. M. Janckowicz, H. A. Nash, D. L. Wise, J. B. Gregory; *Contraception*, 8, 227; 1973). Copolymers of lactic and glycolic acids have also been tested in this context as excipients for injectable or implantable antimalarial drugs (D. L. Wise, G. J. Mc-Cormick, G. P. Willit, L. C. Anderson; *Life Science*, 19, 867; 1976) as well as for the naicetic antagonist naltrexone; A. D. Schwope, D. L. Wise, J. F. Howes, *Life Sciences*, 17 1877; 1976.

Although many matrix devices for sustaining the delivery of drugs in vivo utilize biodegradable excipients, this is not a requirement. Weiner & Johansson (E. Weiner, E. D. B. Johansson; *Contraception*, 14, 551; 1976) implanted subcutaneously silastic rods impregnated with d-norgestrel in four women. Antiovulatory efficacy was observed for more than one year.

Intravaginal and Intrauterine Devices

A variety of mechanical devices for placement within the female reproductive tract are available which act to prevent fertilization of the ovum or implantation of the blastocyst. These are broadly divided into two classes; vaginal and intrauterine (intrafundal) devices (IUD). No presently available device utilizing the cervical canal is known to exist.

Vaginal contraceptive devices which prevent upward migration of sperm past the cervix are placed in the vaginal canal to block the external os of the cervix. An example of this is a diaphragm which was invented prior to 1882 by the German physician W. P. J. Mensinga and is still in use with only minor modification (Contraceptive Technology: Current and Prospective Methods. S. J. Segal and C. Tietze, Reports on Population/Family Planning, October, 1969). The intent is two-fold: not only to seal off the cervix but more importantly to be a vehicle to ensure that spermicide (foam, cream, jelly, etc.) is placed between the cervix and the site of sperm deposition. With the increased availability of oral and parenteral steroidal contraceptives and of intrauterine (intrafundal) devices (IUD's), the diaphragm is now less commonly the first choice of contraceptives among women.

IUD's (intrafundal devices) were patented and used in the 19th century to interfere with fertilization and/or nidation. In the first half of the 20th century devices of silver, gold, or stainless steel were introduced by Grafenberg in Germany; Haire and Jackson in England; Knock in Indonesia; and Ota in Japan (Reproduction in Mammals, Ed. C. R. Austin and R. V. Short, Ch. 2, "Limiting Human Reproductive Potential," D. M. Potts, Cambridge Univ. Press., 1972, Cambridge, England, p. 32ff). Currently a variety of flexible plastic IUD's are available. The Lippes Loop is widely used throughout the world as is the Margulies Coil. Other design modifications include the Tatum T, Saf-T-Coil, double Coil, Dalkon Shield, etc. Copper has been included in some to improve efficacy. The Copper-7 is a slight modification of the Tatum Copper-T. Other devices including copper are also available; all use metallic copper wound as fine wire external to some portion of the device.

The higher pregnancy rate, higher expulsion and removal rates with some devices such as the large spiral or ring indicate that these are less acceptable than the loop or double coil. The Majzlin stainless steel spring has been effective but, as with the Dalkon shield, it is sometimes difficult to remove. The Dalkon shield was developed because evidence suggests that the surface area in contact with the endometrium determines the contraceptive effectiveness (Reproduction in Mammals, Ed. C. R. Austin and R. V. Short, Ch. 2, "Limiting Human Reproductive Potential," D. M. Potts, Cambridge Univ. Press., 1972, Cambridge, England, p. 32ff). Both of these devices are no longer in use, not only because of the difficulty of removal but more importantly because of penetration of the uterine wall.

The addition of copper to the IUD decreases the pregnancy rate associated with the device (Human Reproduction; E. W. Page, C. A. Villee, D. B. Villee, W. B. Saunders Co., Phil.; 1972, pp. 90,91). Tests using rabbits have shown that copper wires depress implantation rates when placed in the inferior portion of one uterine horn near the cervical os. Silver, tin, or magnesium did not show this effect (J. A. Zipper, M. Medal, R. Prager; *Am. J. Obs. Gyn.;* 105, 529; 1969). The use of copper in the "T" device has also been shown to increase contraceptive efficacy in the human (J. A. Zipper, H. J. Tatum, L. Pastene, M. Medel, M. Rivera, *Am. J. Obs. Gyn.;* 105, 1274; 1969). Corrosion of copper-7 IUD's has been studied by Archer et al (K. M. Lewis, R. D. Archer, A. P. Ginsbert, A. Rosencweig, *Contraception*, 15, 93; 1977). In situ corrosion of the copper gives rise to depositions in the corrosion layer consisting mainly of Cu(I) and Cu(II) species with lesser amounts of iron and other components. Analytical results indicate that the oxidation is caused by molecular oxygen and not by oxidized glutathione as previously suggested.

The efficacy of IUD's is increased not only by the presence of copper but also by the bulk of the device, or by the area in contact with the uterine endometrium. However, IUD's are not without attendant difficulties. The average monthly blood loss among IUD users is 38.2 ml as compared with 16.3 ml for control groups and 12.0 ml for women using oral (steroidal) contraceptives. Other difficulties encountered in the use of IUD's include the risk of infection, cramps, and in poorly designed IUD's the danger of penetration of the uterine wall.

SUMMARY OF THE INVENTION

The primary object of the present invention is to provide an improved contraceptive device, useful over an extended period of time, for prohibiting the migration of sperm into the fundus of the uterus.

Another object of the invention is to provide an apparatus consisting of two parts wherein all of the essential portions thereof fit into and operate from the cervical canal.

Another object is to provide an apparatus consisting of two parts; the first part to be a semi-permanent anchoring device to which can be attached a replaceable structure that will contain various, usually depletable, agents to which the cervical canal will be continuously exposed as long as a supply of the agent remains within the attached device. This attached portion is characterized by its being easily replaced periodically without discomfort or danger to the user.

Another object is to provide an apparatus consisting of two parts wherein the second part may be attached to the first part (ICC) by magnets, thus allowing easy removal and replacement of the second part.

Another object is to include, in the replaceable structure, an agent which will enhance the contraceptive properties of the device. Such an agent, for example, can be a metal such as copper, or suitable compounds thereof, to which the cervical canal will be continuously exposed for as long as the metal remains. This agent can be contained in a ribbon of polymeric matrix attached, for example, to a magnetic head.

Still another object of the invention is to provide, from a ribbon of polymeric matrix, the sustained release of a pathogenocide such as vibramycin which will protect the user from the upward extension of venereal infections.

A further object of the invention is to provide in the replaceable part the capacity for sustained release of other drugs such as steroids, for additional contraceptive protection or for other therapeutic purposes.

Further objects of the invention include the novel process for use of the novel apparatus disclosed above.

Other objects of the invention will be obvious to those skilled in the art on their reading of this disclosure.

The above objects are substantially achieved by utilization of a novel structure to be contained within the human cervical canal for the dual purposes of prevention of venereal infections and of contraception. The structure described herein is neither a vaginal barrier device nor an IUD. Its location within the female reproductive tract is entirely within the cervical canal except for a thread depending therefrom the facilitate removal. Such a device is best termed an intracervical cuff (ICC).

The ICC, with its attendant contraceptive and pathogenocidal attachments, will control the migration of sperm and the spread of gonorrhea, mycoplasma, and the less common sexually contracted diseases, as well as possibly prevent syphilitic infection. Since the cervical canal is the "bottleneck" of the female reproductive system, the contraceptive attack is totally local and confined within a small region. The contraceptive action is without the systemic effects associated with the use of such materials as oral or parenteral (injected) contraceptives. Moreover, since the ICC is fitted within the cervical canal, the risks of fundal perforation, endometrial and tubal infection, and bleeding caused by trauma to the endometrium or to fibroids will be eliminated.

Thus, Applicants have developed a device in two parts. Part A is a semi-permanent, intracervical cuff (ICC), an apparatus sized to fit into and function within the human cervical canal. Different sizes will be needed depending on the degree of parity. Part A comprises a central member with a channel through it and positioning members which form the means to maintain the cuff in place by bearing outwardly against the cervical canal wall. These positioning members, which may have stabilizing prongs, are retractable, e.g. as by elongation of the cuff structure, and thereby need not interfere with insertion or—if necessary—removal of the cuff. The cuff member advantageously comprises means to hold Part B, a medicament-bearing temporary member, in a manner which allows the medicament-bearing member to be released and replaced whenever necessary. A magnetic attachment between a relatively permanent cuff member and the medicament bearing means is a convenient attachment technique which requires minimal structure.

Channels in the central member and medicament dispensing means should provide for a continuous drainage conduit. It is preferred that the channels be apertures in the mid-axis of the cervical canal.

Illustrative Embodiment of the Invention

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

IN THE DRAWINGS

FIG. 4 is an illustration of the applicator useful in placement of the apparatus of FIGS. 1 through 3 in the cervical canal.

FIG. 5 illustrates the ICC in extended configuration mounted on the applicator.

FIG. 6 is an elevation, fragmentary and partially in section, of a medicated magnetic insert in position on the applicator rod for insertion in the cervical canal.

Figure 1:
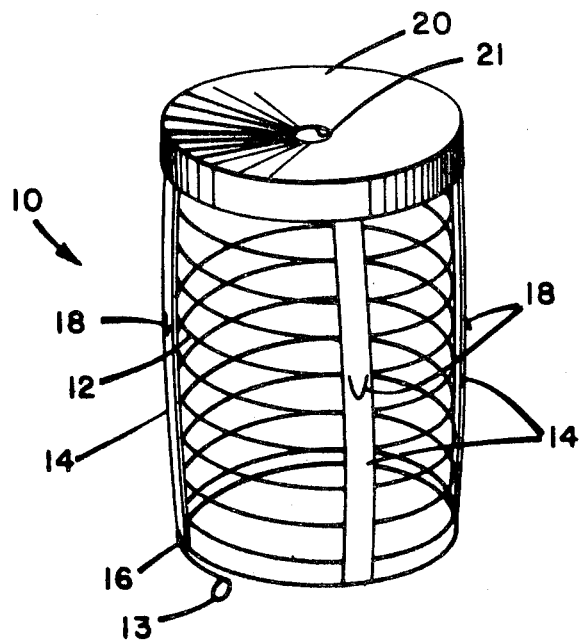
FIG. 1 is a perspective view of an ICC in its extended configuration ready for insertion.
Figure 2:
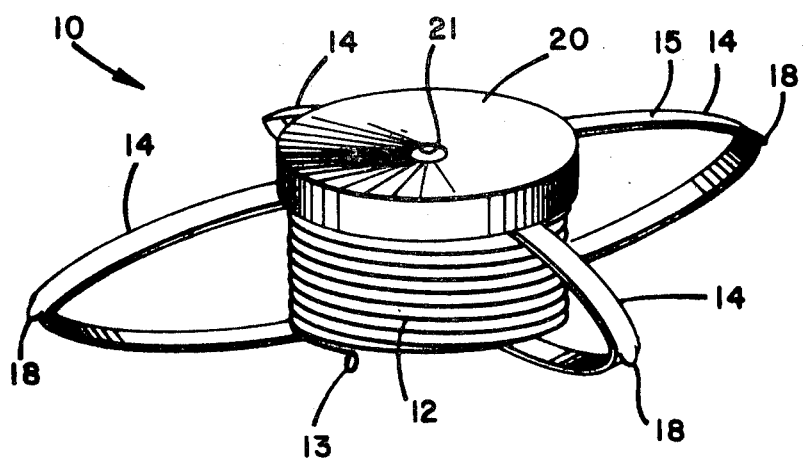
FIG. 2 is a view of the apparatus of FIG. 1 at equilibrium, i.e. in its normally closed configuration.

Referring to FIGS. 1 and 2, the ICC 10 consists of a coiled helical spring 12 of stainless steel which in its equilibrium position (see FIG. 2) assumes a minimum length $l_e$. External to the spring 12 are affixed a plurality of flat spring strips 14 of plastic or metal which form means to hold the ICC 10 properly positioned within the cervical canal. Each strip 14 is fastened at its ends 16 to the upper and lower portions of spring 12 so that when extended the strips 14 lie in planes approximately parallel to the axis of the helix formed by the spring 12. Spring 12 also comprises an eye 13 at the lower end thereof. In the spring's extended configuration (FIG. 1) strips 14 are pulled straight and lie against, or close to, spring 12. When the spring 12 is allowed to assume its equilibrium position the strips bend outwardly to assume a bowed shape. The outer surface 15 of these strips may bear one or more studs or prongs 18 or similar position-stabilizing means. When in bowed position the strips 14 will press against the wall of the cervical canal and the studs 18 will help to maintain the proper orientation of the cuff 10 within the cervical canal.

To the fundal end of the spring 12 is affixed a ring shaped magnet 20, the axis of which is coincident with the axis of the spring. There is a central aperture 21 in the magnet 20 to allow drainage. Magnet 20 forms a central member and is the primary mechanical barrier means of the ICC structure. The entire device can be coated with a plasic material such as polyethylene or a polytetrafluoroethylene-type material.

Although the illustrated device is spring operated, the maximum diameter of the device as measured perpendicular to the axis of the spring advantageously will not exceed $d+(l^2-l_e^2)^{\frac{1}{2}}$ where d is the diameter of the helical spring; $l_e$ is the equilibrium length of the spring; and l is the length of the strip 14. Thus, for example, if $d=l_e$ and $l=2\, l_e$, the maximum extension preferably will not exceed 2.73 $l_e$. Greater diameters on expansion can be achieved by increasing the ratio $l/l_e$. If, once again, $d=l_e$ but $l-3\, l_e$ then the maximum extension will not exceed 3.83 $l_e$. Thus several sizes may easily be manufactured using springs of the same diameter, d, but which can be extended to different lengths, l. the fully extended length may be determined by the length of the strip affixed to the spring.

Figure 3:
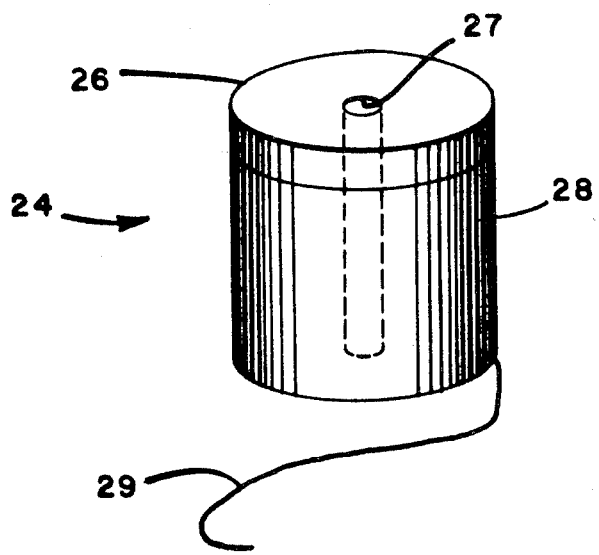
FIG. 3 is an illustration of a magnetically-attachable insert member useful in practice of the invention.

As seen in FIGS. 2, 3 and 6, the full potential of the ICC can be realized by inserting into the lower end 22 of the spring a temporary insert member 24 which contains an active agent or mixture of agents such as some metal or metal-bearing compounds, spermicidal and pathogenocidal agents such Vibramycin, and a steroid or some other drug. Member 24 comprises a magnet 26 forming the top thereof and fastened thereto, a polymer-based sustained release member 28. Magnet 26 is tapered and also apertured to provide a central channel for uterine drainage. The purpose of this insert member 24 is to provide a release of the active agent over an extended period of time. This insert member comprises a ring shaped magnet 26 similar to that which is affixed to the uterine end of the spring on the cuff member 10. To this magnet 26 is fastened an insert, i.e. a hollow cylinder of polymer release member 28 which can serve as an excipient for metal and/or drug. Thus, magnet 26 forms means to receive and hold a medicament-bearing means. In addition a pull string 29 of a non-biodegradable polymer or other inert material will be affixed to the insert and form means to detach the insert from the permanent ICC member 10. On proper placement of the insert member, the string 29 will hang through the cervical canal for ease of removal. Removal will be effected by merely pulling with a force sufficient to separate magnets 26 and 20.

The dimensions of the insert member will be such as to fit within the coiled spring in its equilibrium configuration. The cylidrical openings in both the insert member and the magnet affixed thereto should be tapered and need be no more than 1–2 mm to allow appropriate drainage of menstrual flow or other uterine fluids.

The polymeric excipient for the metal and the drug can be any polymer or copolymer capable of providing slow and continuous release of these agents by either of the mechanisms previously described. An example is the group of copolymers synthesized from lactide and glycolide.

The physical form of the active agents may vary. The metal, copper for example, may be present as ribbon, wire, powder, or screen imbedded in the polymer. The drug, vibramycin for example, may be incorporated as a finely divided crystalline powder into the matrix or may be present as a solid solution therein or as the crystalline powder in eqilibrium with its solution.

The quantity of active agents contained within the excipient depends in part on the volume available. Representative dimensions of the insert member are as follows: outside diameter, 5 mm; inside diameter, 1 mm; height of polymer collar, 3 mm. The polymer volume is then about 56.5 mm$^3$. One example of a formulation is 25.5 wt% drug, 25.5 wt% polymer, and 49.0 wt% metal to give an approximate weight of 100 mg. If replacement of the insert member is to be on a yearly basis release rates for the drug could be as high as 70 micrograms/day and for the metal 134 micrograms/day. Drug release rates of about 10 micrograms/day are estimated as sufficient and may be controlled by variations of polymer loadings and molecular weight.

As seen in FIG. 4, applicator 38 can be used to serve the dual purpose of placing the ICC within the cervical canal and for placing the insert within the ICC. Applicator 38 is formed of an external hollow plastic tube 39 with a flange 41 placed several millimeters below its lip to control the distance the device enters the cervical canal. On the lip 43 of the tube 39 a small hook 48 is located tangent to the rim to engage an eye 13 at the lower end of the spring. Into this tube is inserted a solid shaft 40. The top section, i.e. the tapered 42 of shaft 40, as seen in FIGS. 4 and 6, has a diameter sufficient to fit through the apertures 21 and 27 in the magnet 20 of the ICC and magnet 26 of insert 24. The portion 44 of the rod beneath the tip 42 is so sized to enter the coil of the spring and to bear upwardly against the magnet 26 during insertion.

Part One of the device is placed on the stepped applicator shaft 40 and the eye 13 of the ICC is engaged with a hook 48 of applicator 38, best seen in FIG. 4. Thereupon, finger grips 60 are used to push the applicator shaft 40 upwardly, thereby extending the spring 12 and straighting the strips 14. In this straightened configuration the device is ready for insertion. When compression is released the ICC tends to be pulled into the position shown in FIG. 2, i.e. towards its equilibrium configuration. The hook and eye are readily disengaged by a partial twist and the applicator may be removed.

A magnetic insert member Part Two is then placed on section 42 of the stepped applicator and the applicator is reinserted into the spring which is now in place in the cervical canal. The tapered tip 42 of the applicator shaft 40 will serve as a guide to allow proper positioning. Once the magnet 26 is brought into proximity to magnet 20 magnetic force will keep the insert in place. The insert may be removed merely by pulling the attached string 29 which hangs through the cervical canal. Periodic replacement of the insert is required as its duration of effective action is limited by the rate of release of copper ion, drug, or the like from the matrix.

It is also to be understood that the following claims are intended to cover all of the generic and specific features of the invention herein described and all statements of the scope of the invention which might be said to fall therebetween.

What is claimed is:

1. An intracervical apparatus, sized to function wholly within the cervical canal, and consisting of an apertured central member and laterally-moveable positioning members attached to said means, said positioning members forming means to move outwardly and push outwardly, as against the walls of the said cervical canal, and form means to hold said apparatus in a substantial fixed intracervical position and wherein said apparatus comprises a medicant-bearing material forming means to dispense medicane into said cervical canal and wherein said positioning means is formed of a coiled spring attached to said central member and flexible positioning means connected to said spring, said spring forming means to keep said flexible positioning member in a normal position in which they are bowed outwardly from said coil and said spring forming means, when extended, to pull said flexible positioning members inwardly toward the coil.

2. An intracervical device as defined in either of claim 1 comprising means to receive and hold a medicament-bearing means.

3. An intracervical device as defined in claim 2 wherein said means to receive and hold a medicament-bearing means is a magnet.

4. Apparatus as defined in, any of claims 2, 3 or 4 wherein said apparatus comprises a medicament-bearing means detachably carried on said intracervical apparatus.

5. Apparatus as defined in claim 4 wherein said medicament-bearing means carries a magnet attachable to said apertured central member.

6. Apparatus as defined in claim 5 wherein said medicament-bearing means has an aperture which is co-axial with the aperture of the apertured central member.

7. Apparatus as defined in claim 2 wherein said medicament-bearing means has an aperture which is co-axial with the aperture of the apertured central member.

8. A process for providing efficient long term protection of the uterus against pathogenic organisms comprising the steps of a. implanting, substantially within the cervical canal, a physical central member comprising chemical barrier means to prevent passage of said pathogenic organisms and b. providing within said central member an open channel effective to assure drainage of uterine wastes and wherein said means to prevent passage of said pathogenic organisms means to release active pathogenocidal agents over a prolonged period of time and comprising the additional steps of removing and replacing said sustained release device while leaving said physical central member in the cervical canal.

9. A process as described in claim 8 comprising the step of magnetically attaching a sustained release device to said central member.

10. Apparatus for placing an intracervical device within the cervical canal, said apparatus comprising
   (1) an intracervical cuff to be placed within said cervical canal;
   (2) an internal applicator member forming means for supporting said intracervical cuff and for positioning said intracervical cuff within said intracervical canal;
   (3) an external applicator member forming a sleeve in which said internal applicator member is mounted for movement with respect to said external applicator;
   (4) a flange on the outer wall of said sleeve, said flange forming means to limit movement of said internal applicator into internal applicator member into a cervical canal.

11. Apparatus as defined in claim 10 wherein said internal applicator means is stepped in diameter and comprises (1) a thinner tapered tip portion to receive an apertured central member and (2) a thicker portion below said tip portion to receive an intracervical cuff adapted to receive said central member.

12. Apparatus as defined in claims 10 or 11 wherein said external member, and said intracervical cuff, comprises attachment and release means to facilitate placement and removal of said intracervical cuff in said cervical canal.

13. Apparatus as defined in claim 1 wherein said apparatus comprises a medicament-bearing means detachably carried on said intracervical apparatus.

14. Apparatus as defined in claim 2 wherein said apparatus comprises a medicament-bearing means detachably carried on said intracervical apparatus.

15. Apparatus as defined in claim 3 wherein said apparatus comprises a medicament-bearing means detachably carried on said intracervical apparatus.

16. Apparatus as defined in claim 1 wherein said medicament-bearing means has an aperture which is co-axial with the aperture of the apertured central member.

17. Apparatus as defined in claim 2 wherein said medicament-bearing means has an aperture which is co-axial with the aperture of the apertured central member.

18. Apparatus as defined in claim 3 wherein said medicament-bearing means has an aperture which is co-axial with the aperture of the apertured central member.

19. Apparatus as defined in claim 3 wherein said medicament-bearing means forms means to sustain the release of said medicament over an extended period of time.

20. Apparatus as defined in claim 4 wherein said medicament-bearing means forms means to sustain the release of said medicament over an extended period of time.

21. Apparatus as defined in claim 5 wherein said medicament-bearing means forms means to sustain the release of said medicament over an extended period of time.

22. Apparatus as defined in claim 7 wherein said medicament-bearing means forms means to sustain the release of said medicament over an extended period of time.

23. Apparatus as defined in claim 4 wherein said medicament-bearing means has an aperture which is co-axial with the aperture of the apertured central member.

* * * * *